United States Patent
Jiang

(10) Patent No.: US 9,974,153 B2
(45) Date of Patent: May 15, 2018

(54) CONTROLLING FILAMENT CURRENT OF COMPUTED TOMOGRAPHY TUBE

(71) Applicant: SHENYANG NEUSOFT MEDICAL SYSTEMS CO., LTD., Shenyang (CN)

(72) Inventor: Zhewen Jiang, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 209 days.

(21) Appl. No.: 14/864,620

(22) Filed: Sep. 24, 2015

(65) Prior Publication Data

US 2016/0088718 A1     Mar. 24, 2016

(30) Foreign Application Priority Data

Sep. 24, 2014   (CN) .......................... 2014 1 0494104

(51) Int. Cl.
| | |
|---|---|
| A61B 6/03 | (2006.01) |
| H05G 1/08 | (2006.01) |
| H05G 1/26 | (2006.01) |
| H05G 1/30 | (2006.01) |
| H05G 1/34 | (2006.01) |
| H05G 1/32 | (2006.01) |

(52) U.S. Cl.
CPC .................. *H05G 1/34* (2013.01); *H05G 1/08* (2013.01); *H05G 1/085* (2013.01); *H05G 1/26* (2013.01); *H05G 1/265* (2013.01); *H05G 1/30* (2013.01); *H05G 1/32* (2013.01); *A61B 6/032* (2013.01)

(58) Field of Classification Search
CPC ............ H05G 1/08; H05G 1/085; H05G 1/26; H05G 1/265; H05G 1/30; H05G 1/34; A61B 6/032

USPC ...................................... 378/16, 91, 108–110
See application file for complete search history.

(56) References Cited

U.S. PATENT DOCUMENTS

| | | | | |
|---|---|---|---|---|
| 2,728,862 | A | * | 12/1955 | De Bourgknecht .... G01T 1/185 250/388 |
| 3,983,396 | A | * | 9/1976 | Mulleneers .............. H05G 1/34 378/101 |
| 4,072,865 | A | | 2/1978 | Craig et al. |
| 4,104,526 | A | * | 8/1978 | Albert .................. G01N 23/223 378/106 |

(Continued)

FOREIGN PATENT DOCUMENTS

| | | |
|---|---|---|
| CN | 1048780 A | 1/1991 |
| CN | 102483638 A | 5/2012 |

(Continued)

*Primary Examiner* — Allen C. Ho
(74) *Attorney, Agent, or Firm* — McCoy Russell LLP

(57) ABSTRACT

A method for controlling filament current of a computed tomography (CT) tube includes: detecting a present tube current of the CT tube and assigning the present tube current to a feedback value, calculating a difference between a set value of the tube current and the feedback value and assigning the difference to an error value, assigning a target upper bound value to a present filament current when the error value is greater than an first error threshold, and assigning a target lower bound value to the present filament current when the error value is less than a second error threshold, wherein the target upper bound value is greater than the target lower bound value, the first error threshold is greater than 0, and the second error threshold is less than 0.

12 Claims, 10 Drawing Sheets

(56) References Cited

U.S. PATENT DOCUMENTS

| | | | | |
|---|---|---|---|---|
| 4,177,406 A * | 12/1979 | Hermeyer | | H05G 1/34 378/110 |
| 4,311,913 A * | 1/1982 | Resnick | | H05G 1/34 378/101 |
| 4,322,797 A * | 3/1982 | Lickel | | H05G 1/34 378/110 |
| 4,361,901 A * | 11/1982 | Daniels | | A61B 6/02 257/10 |
| 4,376,894 A * | 3/1983 | Vogler | | H02P 23/08 318/727 |
| 4,596,029 A * | 6/1986 | Manueco Santurtun | | H05G 1/32 378/105 |
| 4,601,051 A * | 7/1986 | Santurtun | | H05G 1/32 378/105 |
| 4,654,770 A * | 3/1987 | Santurtun | | H05G 1/34 361/93.9 |
| 4,703,496 A * | 10/1987 | Meccariello | | H04N 5/32 348/E5.086 |
| 4,768,216 A * | 8/1988 | Harvey | | H05G 1/265 363/17 |
| 4,775,992 A * | 10/1988 | Resnick | | H05G 1/34 378/109 |
| 4,797,907 A * | 1/1989 | Anderton | | H05G 1/10 378/101 |
| 4,930,146 A * | 5/1990 | Flakas | | H05G 1/34 378/109 |
| 5,001,735 A * | 3/1991 | Sammon | | H05G 1/46 378/110 |
| 5,077,773 A * | 12/1991 | Sammon | | H05G 1/46 378/109 |
| 5,111,493 A * | 5/1992 | Siedband | | H01J 35/16 378/102 |
| 5,708,694 A * | 1/1998 | Beyerlein | | H05G 1/34 378/109 |
| 6,738,275 B1 * | 5/2004 | Beland | | H02M 1/088 363/21.02 |
| 6,754,307 B2 * | 6/2004 | Brendler | | H05G 1/46 378/108 |
| 7,023,960 B2 * | 4/2006 | Chretien | | H05G 1/34 378/109 |
| 7,079,622 B2 * | 7/2006 | Chretien | | H05G 1/34 378/109 |
| 7,142,630 B2 * | 11/2006 | Suzuki | | A61B 6/032 378/16 |
| 7,177,392 B2 * | 2/2007 | Shefer | | H05G 1/30 378/108 |
| 7,366,283 B2 * | 4/2008 | Carlson | | H05G 1/46 378/108 |
| 7,529,346 B2 * | 5/2009 | Gaudin | | H01J 35/14 378/138 |
| 7,639,784 B2 * | 12/2009 | Feda | | G01N 23/223 378/106 |
| 7,715,520 B2 * | 5/2010 | Nagata | | A61B 6/032 378/16 |
| 7,764,766 B2 * | 7/2010 | Fujii | | A61B 6/00 378/114 |
| 7,885,384 B2 * | 2/2011 | Mannar | | A61B 6/586 378/118 |
| 7,924,981 B2 * | 4/2011 | Iijima | | H05G 1/12 378/110 |
| 8,265,227 B2 * | 9/2012 | Boudry | | H05G 1/46 378/110 |
| 8,320,521 B2 * | 11/2012 | Zou | | H01J 35/045 378/106 |
| 8,396,185 B2 * | 3/2013 | Zou | | A61B 6/032 378/112 |
| 8,487,534 B2 * | 7/2013 | Caiafa | | H05G 1/32 315/111.31 |
| 8,964,940 B2 * | 2/2015 | Caruso | | H05G 1/34 378/101 |
| 9,050,058 B2 * | 6/2015 | Uebayashi | | A61B 6/54 |
| 9,326,740 B2 * | 5/2016 | Watanabe | | H05G 1/265 |
| 9,338,868 B2 * | 5/2016 | Yabugami | | H05G 1/32 |
| 9,592,023 B2 * | 3/2017 | Tanaka | | A61B 6/032 |
| 9,844,357 B2 * | 12/2017 | Lee | | A61B 6/542 |
| 9,867,590 B2 * | 1/2018 | Tamura | | A61B 6/585 |
| 2004/0109536 A1 | 6/2004 | Shefer et al. | | |
| 2014/0140474 A1 | 5/2014 | Caruso et al. | | |

FOREIGN PATENT DOCUMENTS

| | | |
|---|---|---|
| CN | 102483638A A | 5/2012 |
| CN | 102612248 A | 7/2012 |
| JP | H0193098 A | 4/1989 |
| JP | H08195294 A | 7/1996 |
| JP | 2011-238446 A | 11/2011 |
| JP | 2014018365 A | 2/2014 |

* cited by examiner

US 9,974,153 B2

CONTROLLING FILAMENT CURRENT OF COMPUTED TOMOGRAPHY TUBE

CROSS-REFERENCE TO RELATED APPLICATIONS

The present application claims priority to Chinese Patent Application No. 201410494104.2, filed on Sep. 24, 2014, the entire contents of which are hereby incorporated by reference for all purposes.

BACKGROUND

Computer tomography (CT) apparatus is a medical diagnostic equipment. The CT apparatus may use an X-ray to pass through a subject (e.g. a patient) and receive the X-ray that passes through the subject. A received X-ray may form an image rendering morphology of internal organs of the subject. In the CT apparatus, X-rays are generated and emitted by a CT tube which is also known as an X-ray tube.

The CT tube is actually a high-vacuum cathode-ray diode having a cathode and an anode, wherein a filament is deployed at the cathode. When the CT tube is in a work mode, a current may be provided to the filament through the cathode for heating the filament to generate a gathered free electron cloud. High voltage may be applied between the cathode and the anode, abruptly increasing an electric potential between the cathode and the anode. Owing to a strong electric field at high voltage, a free electron beam in an active state at the filament of the cathode may strike a tungsten target in a molybdenum base at the anode, and energy transformation may occur. Part of the electrical energy may be converted into X-rays and emitted through a window, and another part of the electrical energy may be converted into heat which is dissipated by a cooling system. The current provided to the filament at the cathode is called filament current. The voltage between the cathode and the anode is called tube voltage. The electrons generated by heating the filament may move at high-speed from the cathode to the anode under the high voltage potential, and form a current called tube current. The present disclosure pertains to controlling the filament current of the CT tube so as to implement X-ray radiation dose control of the CT equipment.

Neusoft Medical Systems Co., Ltd. (NMS), founded in 1998 with its world headquarters in China, is a leading supplier of medical equipment, medical IT solutions, and healthcare services. NMS supplies medical equipments with a wide portfolio, including CT, MRI, digital X-ray machine, Ultrasound, PET (Positron Emission Tomography), Linear Accelerator, and Biochemistry Analyzer. Currently, NMS' products are exported to over 60 countries and regions around the globe, serving more than 5,000 renowned customers. NMS' latest successful developments, such as 128 Multi-Slice CT Scanner System, Superconducting MRI, Linear Accelerator, and PET products, have led China to become a global high-end medical equipment producer. As an integrated supplier with extensive experience in large medical equipment, NMS has been committed to the study of avoiding secondary potential harm caused by excessive X-ray irradiation to the subject during CT scanning process.

BRIEF DESCRIPTION OF DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Currently, adjustment of X-ray radiation of a computer tomography (CT) equipment may be typically implemented by controlling the tube current of a CT tube. The tube current of a CT tube may be adjusted by controlling the filament current. In general, the larger the filament current, the higher the temperature of the filament. Thus, the number of electrons which are generated by heating the filament may be increased to emit electrons from the cathode to the anode, and the tube current may also be increased.

Figure 1:
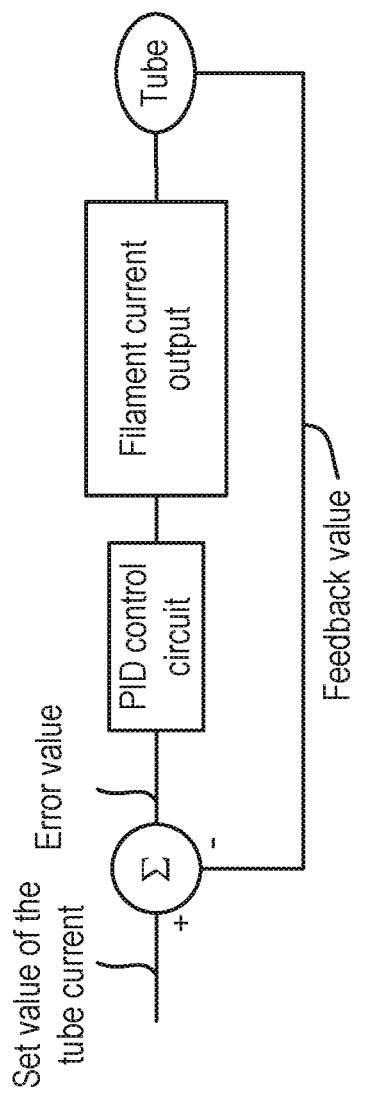
FIG. 1 is a schematic diagram of a filament current control circuit by using proportion, integration, and differentiation (PID), according to an example of the present disclosure.

As shown in FIG. 1, in an example, a target value of a desired tube current may be used as a set value of the tube current, present real detection tube current of the CT tube may be used as a feedback value, and a difference value may be calculated between the set value of the tube current and the feedback value and the difference value may be assigned as error value. The error value may be input into a proportion, integration, and differentiation (PID) control circuit. The PID control circuit may calculate, adjust (for example, linear adjustment) and output the filament current based on the error value. The filament current outputted by the PID control circuit may be provided to the filament of the cathode of the CT tube to eliminate the error value between the set value of the tube current and the feedback value. The error value may be continuously used between the set value of the tube current and the feedback value to adjust the filament current which is provided to filament of the CT tube. Thus, the tube current of the CT tube may be controlled at the set value of the tube current so as to implement the X-ray radiation control of the CT apparatus.

However, in this example, the PID control circuit may be used to calculate the filament current according to the error value of the tube current. The PID control circuit may be a linear operator using a proportion circuit, integration circuit, and differentiation circuit, and it may be very difficult to adjust the parameters of the PID control circuit which may be used to control an outputted filament current. For different CT tubes, usually due to different filament characteristics, parameters of the PID control circuit may also be different. In addition, the PID control circuit may concurrently include proportion, integration, and differentiation (PID), and may simultaneously consider an adjustment of error and a response speed of adjustment. Thus, the filament current outputted by the PID control circuit may be in a linear variation. That is, the outputted filament current may be proportional to the error value of the inputted tube current in a certain ratio. In a variation process of the set value of the tube current, because of a linear variation of the filament current, a variation speed (i.e. dmA/dt) of the real tube current (the feedback value) cannot timely follow the variation of the set value of the tube current. The adjustment speed of radiation dose may be limited, and it may be difficult to achieve rapid adjustment of an X-ray radiation dose.

Figure 3A:
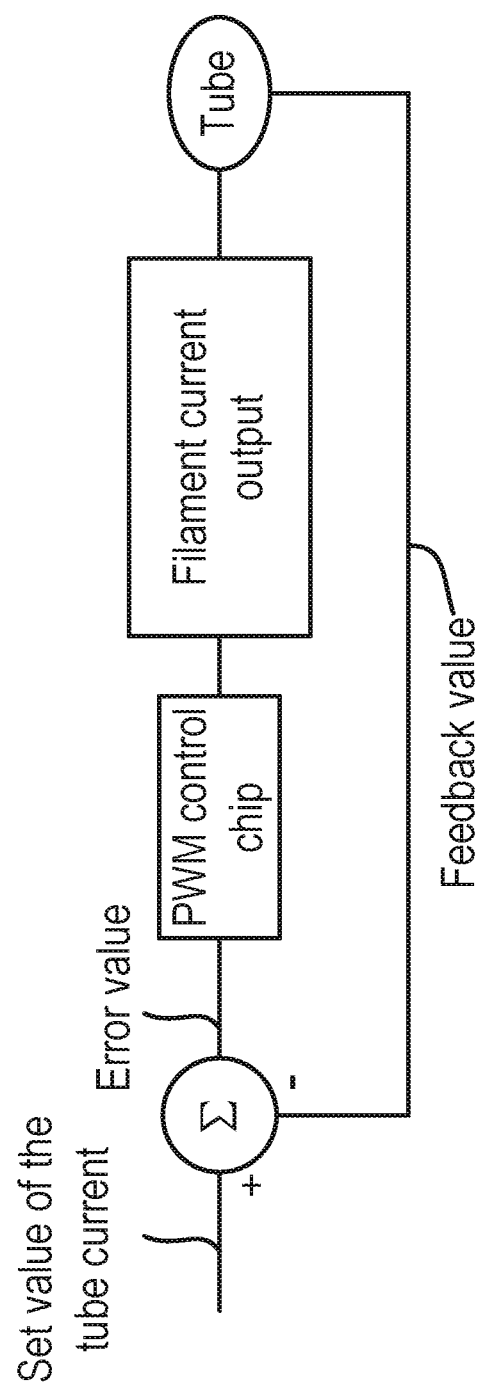
FIG. 3A is a schematic diagram of a pulse width modulation (PWM) chip for controlling filament current, according to an example of the present disclosure.
Figure 3B:
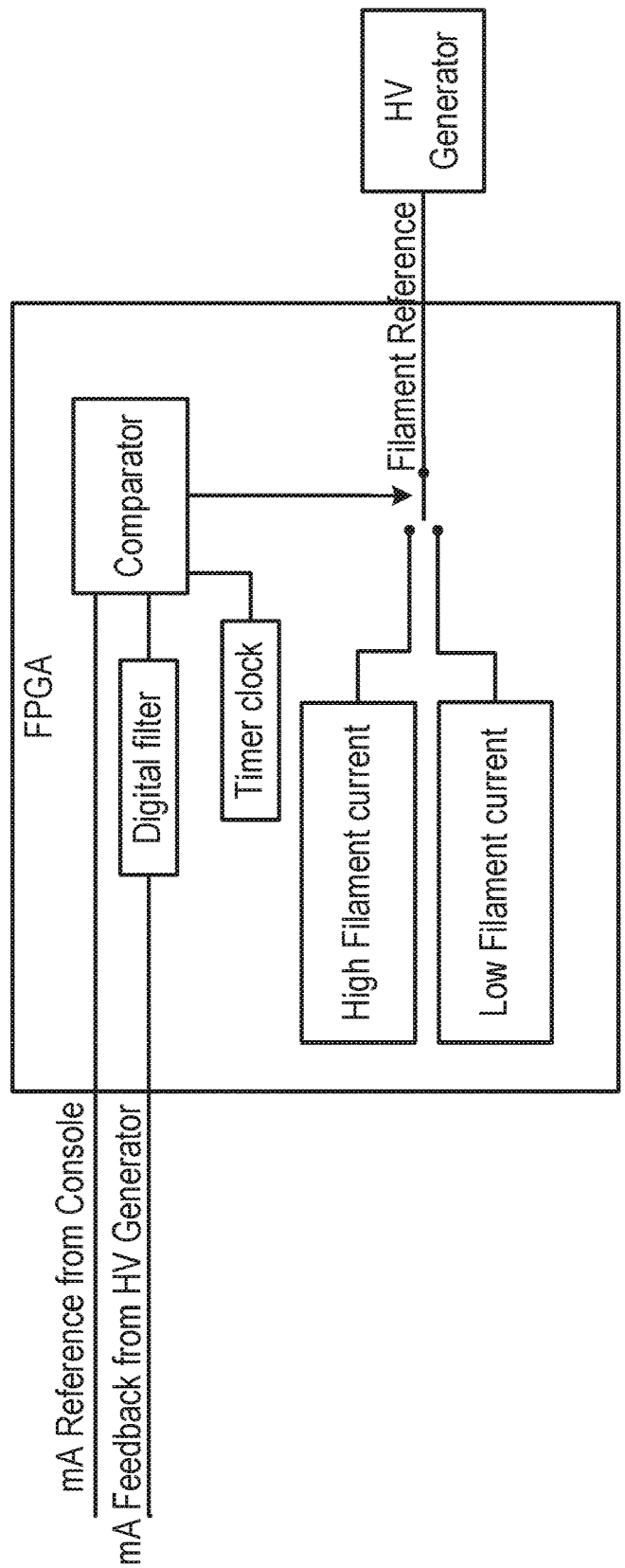
FIG. 3B is a schematic diagram of an internal structure of the PWM chip, according to an example of the present disclosure.

As shown in FIG. 3A and FIG. 3B, in another example, to make the variation of the filament current more quickly, a digital pulse width modulation (PWM) control chip may be used to replace the PID control circuit as shown in FIG. 1. In the PWM control chip which may be implemented by Field-Programmable Gate Array (FPGA) as shown in FIG. 3B, an upper bound value (referenced as High Filament current in FIG. 3B) and a lower bound value (referenced as Low Filament current in FIG. 3B) may be preset in the control range of the filament current to be a target upper bound value and a target lower bound value of the filament current, respectively. By using the error value between the set value of the tube current (referenced as mA Reference from Console in FIG. 3B) and the feedback value (referenced as mA Feedback from HV Generator in FIG. 3B), a comparator in the PWM control chip may control the filament current of the CT tube to switch between the target upper bound value and the target lower bound value. Where, the feedback value may be filtered by a digital filter first and then input into the comparator. When the set value of the tube current may be significantly greater than the feedback value and the error value may be greater than a first error threshold, the PWM control chip may set a present filament current to be the target upper bound value rather than linear increasing. Thus, the real tube current may dramatically increase to follow up the set value of the tube current. When the set value of the tube current may be significantly less than the feedback value and the error value may be less than a second error threshold, the PWM control chip may set the present filament current to be the target lower bound value rather than linear decreasing. Thus, the real tube current may dramatically decrease to follow up the set value of the tube current. In FIG. 3B, a timer clock is used to output a clock signal to the comparator.

Figure 2:
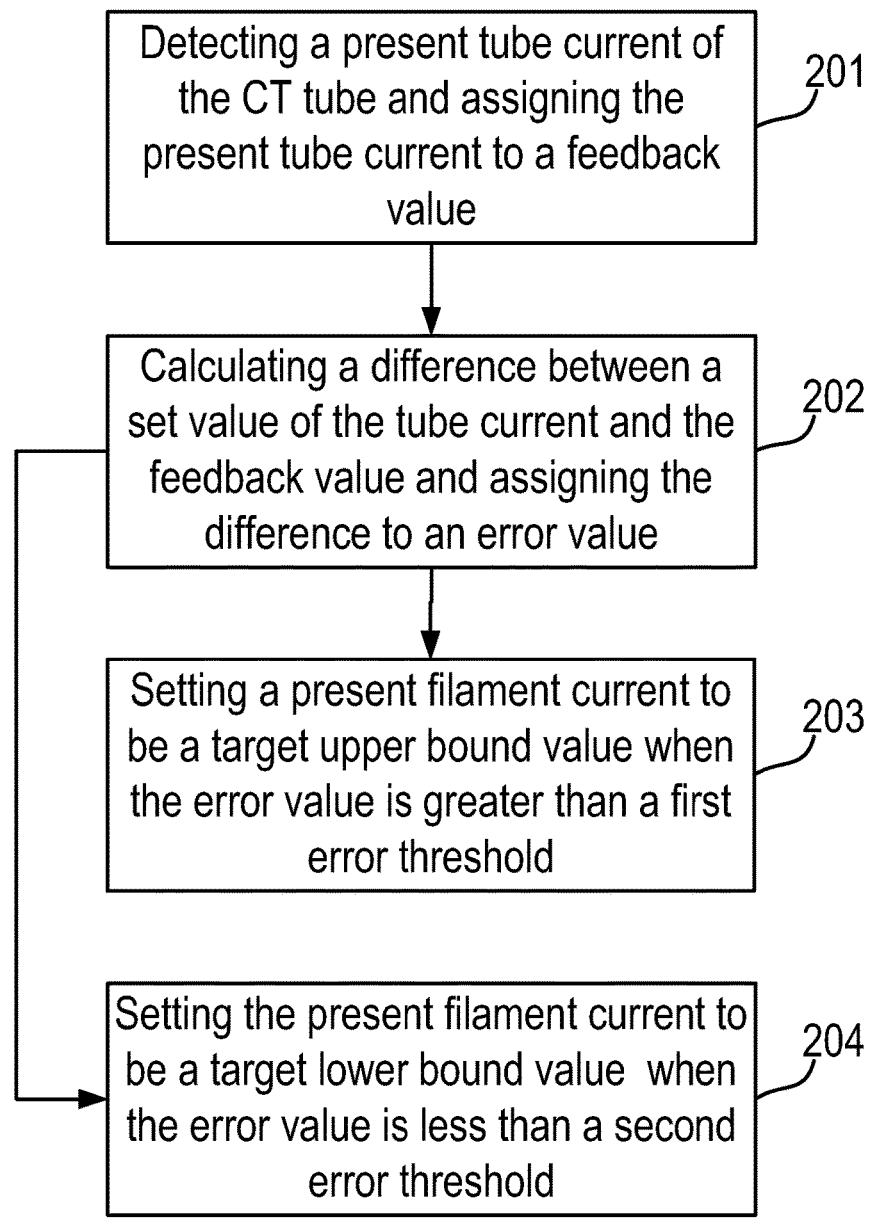
FIG. 2 is a flowchart of a method for controlling filament current of computed tomography (CT) tube, according to an example of the present disclosure.

FIG. 2 is a flowchart of a method for controlling filament current of computed tomography (CT) tube, according to an example of the present disclosure.

In block 201, the method may include detecting a present tube current of the CT tube and assigning the present tube current to a feedback value.

In block 202, the method may include calculating a difference between a set value of the tube current and the feedback value and assigning the difference to an error value.

In block 203, the method may include setting a present filament current to be a target upper bound value when the error value is greater than a first error threshold.

In block 204, the method may include setting the present filament current to be a target lower bound value when the error value is less than a second error threshold.

wherein the target upper bound value is greater than the target lower bound value, the first error threshold is greater than 0, and the second error threshold is less than 0.

Specifically, when the CT tube is in a work mode, the PWM control chip (also be referred as PWM controller thereafter) may detect the tube current of the CT tube to obtain the feedback value of the tube current, calculate a difference between the set value of the tube current and the feedback value, assign the difference to an error value, and input the error value into the PWM controller. The PWM controller may compare a real-time value corresponding to the error value with a first error threshold and a second error threshold, and determine the outputted real-time filament current according to the comparison result. Finally, the PWM controller may output a pulse signal to control the filament current, and adjust the filament current based on the pulse signal, in which the filament current may be inputted into the CT tube. At a specific time during the CT tube being in the work mode, the present real-time value of the feedback signal corresponding to the tube current may be the feedback value of the tube current, the present real-time value of the input signal may be the set value of the tube current, the present real-time value of the error signal may be the error value which is the difference between the set value of the tube current and the feedback value, and the present real-time value of the pulse signal may be used to determine the present filament current which is inputted into the CT tube. In this example, if the error value which is the difference between the set value of the tube current and the feedback value is greater than a first error threshold, then the present real-time value of the pulse signal outputted by the PWM controller may represent a situation that filament current may be the target upper bound value. For example, the present real-time value of the pulse signal may take "1". If the error value is less than a second error threshold, the present real-time value of the pulse signal outputted by the PWM controller may represent a situation that filament current may be the target lower bound value. For example, the present real-time value of the pulse signal may take "0".

In this example, the error value may represent the difference between the set value of the tube current and the feedback value. That is, error value=set value−feedback value, wherein error value may represent the error value between the set value of the tube current and the feedback value, set value may represent the set value of the tube current in advance, and feedback value may represent the present feedback value of the filament current. A first error threshold which compared with the error values may be usually set to greater than 0. A second error threshold which compared with the error values may be usually set to less than 0. When the error value is greater than the first error threshold, it may represent the set value of the tube current and may be significantly greater than the feedback value. In this situation, the real tube current may require to rapidly increase to the set value of the tube current to eliminate the error value between the real tube current and the set value of the tube current. For this reason, it may set the present filament current to be the target upper bound value, in which the target upper bound value is the upper bound of an adjustment range. Thus, the real tube current may be rapidly increased, the error value between the real tube current and the set value of the tube current may be rapidly reduced, and the real tube current may be rapidly followed up the set value of the tube current. When the error value is less than the second error threshold, it may represent the set value of the tube current and may be significantly less than the feedback value. In this situation, the real tube current may require to rapidly reduce to the set value of the tube current to eliminate the error value between the real tube current and the set value of the tube current. For this reason, it may set the present filament current as the target lower bound value, in which the target lower bound value is the lower bound of the adjustment range. Thus, the real tube current may be rapidly reduced, the error value between the real tube current and the set value of the tube current may be rapidly reduced, and the real tube current may be rapidly followed up the set value of the tube current.

In the present disclosure, it should be understood that the control of the filament current may be carried out once every certain period of time. That is, at a regular time interval, it may sample the set value of the tube current and the feedback value, calculate the error value according to the sampled set value and the sampled feedback value, and control the filament current based on the error value. Of course, the control of the filament current may be carried out in continuous style. That is, it may sample the feedback value in real-time to form the continuous feedback signal of the tube current, sample the set value of the tube current in real-time to form the continuous reference input signal of the tube current, calculate the error signal according to the reference input signal of the tube current and the feedback signal of the tube current in real-time, and control the filament current based on the error signal.

In addition, the first error threshold and second error threshold may have the same magnitude and each may have a different sign. For example, the first error threshold may be $\Delta mA$ and the second error threshold may be $-\Delta mA$. Of course, the first error threshold and second error threshold may have different magnitude and each may have a different sign. For example, the first error threshold may be $\Delta mA1$ and the second error threshold may be $-\Delta mA2$. In practical application, the real values of the first error threshold and second error threshold may be dependent on the requirement of the CT image quality, the requirement of the CT equipment accuracy, and so on.

In the present disclosure, when the error value is in a range between the first error threshold and the second error threshold, the control of the filament current may have many different implementations. In an example, when the error value is not greater than the first error threshold and not less than the second error threshold, it may maintain the present filament current unchanged. In another example, when the error value is in the range between the first error threshold and the second error threshold, the variation of the filament may be linear. For example it may set the present filament current to be a multiplication of the error value and a pre-defined control ratio.

It should be understood that the target upper bound value and the target lower bound value of the filament current may be the upper bound value and the lower bound value of the adjustment range of the real filament current in the CT tube. When the error value between the set value of the tube current and the feedback value may be obvious, the filament current may be instantly changed to the upper bound value or the lower bound value of the adjustment range, so that the real tube current may quickly vary to the set value of tube current.

In the present disclosure, it should be understood that the filament current adjustment range may have many different implementations. For example, in an example, the filament current adjustment range may directly be defined based on the filament current corresponding to the tube current upper bound value and the filament current corresponding to the tube current lower bound value. That is, the target upper bound value of the filament current may be the filament current corresponding to the tube current upper bound value of the CT tube, and the target lower bound value of the filament current may be the filament current corresponding to the tube current lower bound value of the CT tube. In other examples, considering the different CT tubes installed in a different application or a different environment, the relationship between the filament current and the tube current may be changed. The adjustment range of the filament current may be determined after calibrating the value of the filament current corresponding to the tube current upper bound value and the value of the filament current corresponding to the tube current lower bound value. That is, the target upper bound value of the filament current may be a calibrated value of the filament current corresponding to the tube current upper bound value, and the target lower bound value of the filament current may be the calibrated value of the filament current corresponding to the tube current lower bound value. In the implementation, the filament current value corresponding to the tube current upper bound value of the CT tube may be assigned to be a target upper bound to be calibrated of the filament current, and the filament current value corresponding to the tube current lower bound value of the CT tube may be assigned to be a target lower bound to be calibrated of the filament current. The target upper bound and the target lower bound may be calibrated to respectively obtain the target upper bound value and the target lower bound value of the filament current.

In the aforementioned examples to obtain the target upper bound value and the target lower bound value of the filament current by calibration, the target upper bound to be calibrated and the target lower bound to be calibrated may be set to be an initial target upper bound value and an initial target lower bound value of the filament current, respectively. In this way, the tube current of the CT tube in the work mode may be initially controlled in a specific set value of the tube current. According to the fluctuation range of the real tube current of the CT tube in the work mode, it may be determined whether adjustments are needed and how to adjust the target upper bound to be calibrated and the target lower bound to be calibrated of the filament current. When there is a need to adjust the target upper bound value and the target lower bound value of the filament current, the target upper bound to be calibrated and the target lower bound to be calibrated may be adjusted to satisfy the requirements of real application. Then, the adjusted target upper bound to be calibrated and the adjusted target lower bound to be calibrated may be identified as the final target upper bound value and the final target lower bound value of the filament current.

Figure 4:
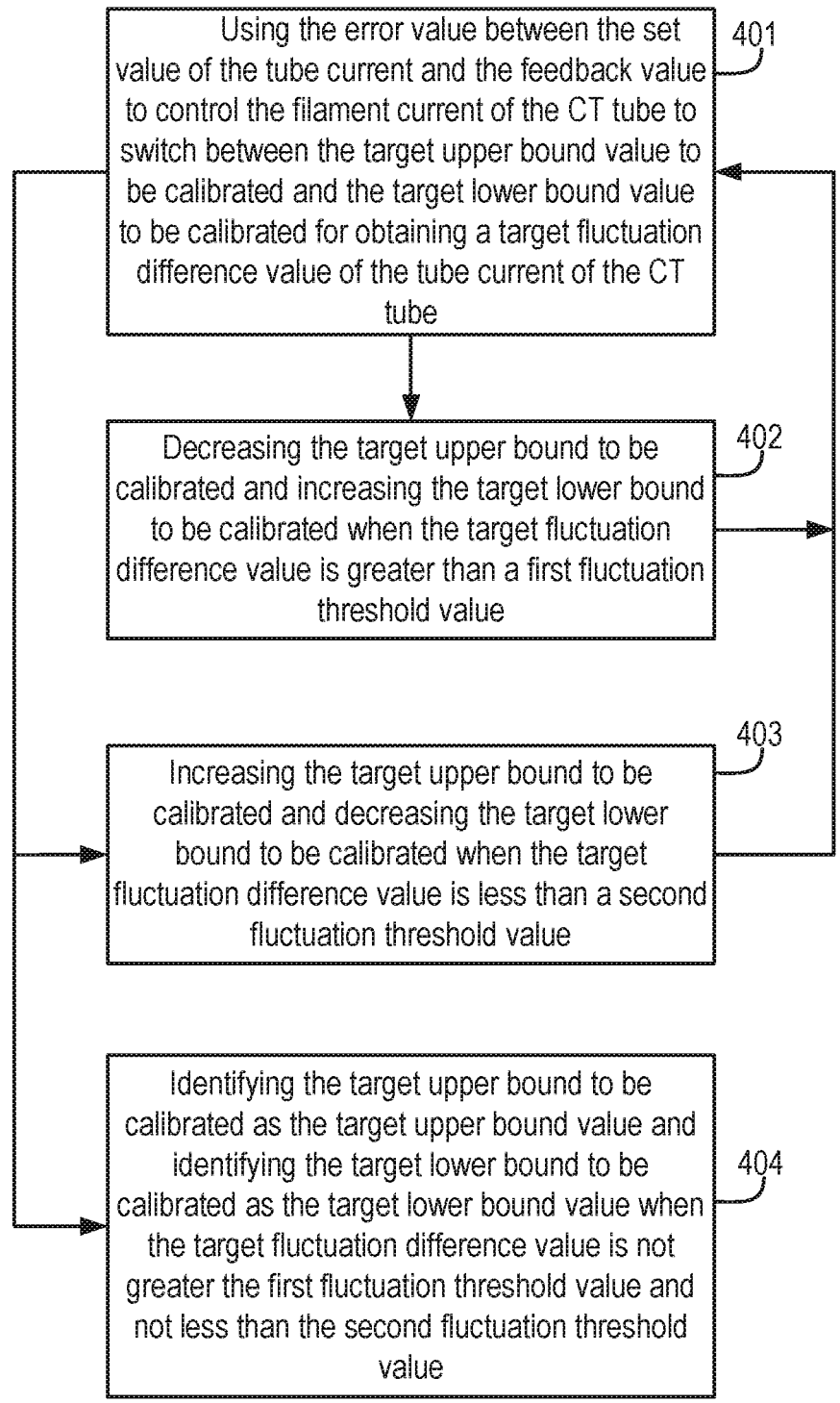
FIG. 4 is a flowchart of a method for calibrating a target upper bound value and a target lower bound value of filament current, according to an example of the present disclosure.

FIG. 4 is a flowchart of a method for calibrating a target upper bound value and a target lower bound value of filament current, according to an example of the present disclosure.

In block 401, the method may include using the error value between the set value of the tube current and the feedback value to control the filament current of the CT tube to switch between the target upper bound to be calibrated and the target lower bound to be calibrated for obtaining a target fluctuation difference value of the tube current of the CT tube. The target fluctuation difference value may be an absolute value of a maximum difference value between the feedback value and the set value of the tube current in the control process.

In this example, in the selection of the set value of the tube current for the calibration and the work process of the control of the CT tube, the tube current may be kept in the set value of the tube current during the CT tube in the work mode. In the control process of the CT tube, according to the comparison result of the error value with the first error threshold or the second error threshold, the filament current of the CT tube may be assigned to the target upper bound to be calibrated or the target lower bound to be calibrated of the present filament current. After the CT tube working for some time under the control, fluctuation of the feedback value of the real tube current of the CT tube in the control process may be obtained. With the fluctuation of the feedback value, the target fluctuation difference value is an absolute value of a maximum difference value between the feedback value and the set value of the tube current in the control process. For calibration purpose, in the control process of the CT tube, the difference between the set value of the tube current and the feedback value may be calculated and the difference is assigned to the error value. When the error value is greater than the first error threshold, the present filament current may be set to be a target upper bound to be calibrated. When the error value is less than the second error threshold, the present filament current may be set to be a target lower bound to be calibrated. When the error value is not greater than the first error threshold and not less than the second error threshold, the set value of the tube current of the present filament current may be unchanged.

In the above mentioned examples of the present disclosure, it should be understood that the main factor of the consideration to make the limitation upon the target upper bound to be calibrated and the target upper lower to be calibrated of the filament current may be the fact that the real tube current will be in a state of fluctuation when the CT tube is in work mode. Thus, in the calibration, for the selection of the set values of the tube current, the tube current upper bound value and the tube current lower bound value may be selected and assigned to the set values of the tube current. Two corresponding fluctuation ranges and two corresponding fluctuation difference values may be obtained and the two fluctuation difference values of each fluctuation range may be compared and the larger fluctuation difference value may be assigned to the target fluctuation difference value. The target fluctuation difference value may be used to determine whether the target upper bound to be calibrated and the target upper lower to be calibrated satisfy the requirement of the upper bound and lower bound of the real tube current of the CT tube in the work mode. Thus the calibration of the upper bound and lower bound of the target current may be made more accurate.

In another example, in block 401, the method may include:

assigning the tube current upper bound value of the CT tube in the work mode to the set value of the tube current, using the error value between the tube current upper bound value and the feedback value to control the filament current of the CT tube to switch between the target upper bound to be calibrated and the target lower bound to be calibrated for obtaining a first fluctuation range of the tube current of the CT tube, and calculating a first fluctuation difference value of the first fluctuation range;

assigning the tube current lower bound value of the CT tube in the work mode to the set value of the tube current, using the error value between the tube current lower bound value and the feedback value to control the filament current of the CT tube to switch between the target upper bound to be calibrated and the target lower bound to be calibrated for obtaining a second fluctuation range of the tube current of the CT tube, and calculating a second fluctuation difference value of the second fluctuation range;

selecting the first fluctuation difference value to be the target fluctuation difference value when first fluctuation difference value is greater than the second fluctuation difference value, or selecting the second fluctuation difference value to be the target fluctuation difference value when first fluctuation difference value is not greater than the second fluctuation difference value.

Figure 5:
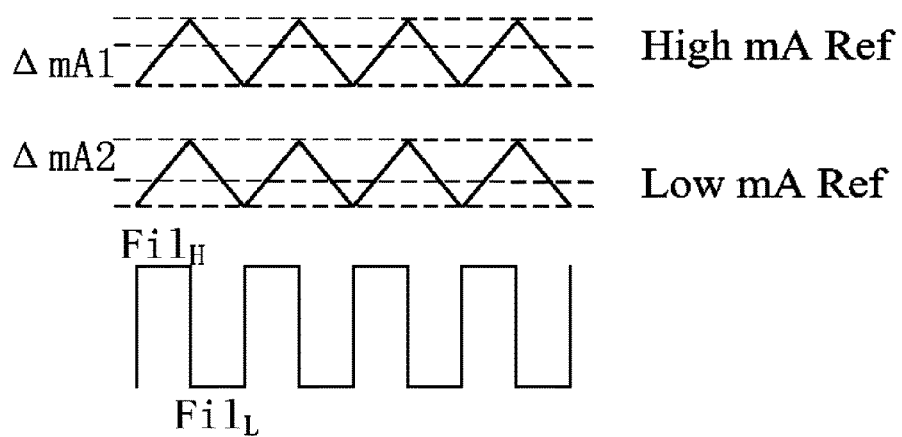
FIG. 5 is a schematic diagram of a fluctuation curve of a real tube current in a calibration process of a filament current, according to an example of the present disclosure.

FIG. 5 is a schematic diagram of a fluctuation curve of the real tube current in the calibration process of the filament current. In the calibration process of the filament current, the tube current upper bound value and the tube current lower bound value may be used as the set values of the tube current in the control process of the CT tube. As shown in FIG. 5, the label "High mA Ref" in FIG. 5 may represent the fluctuation curve of the real tube current in which the tube current upper bound value is assigned as the set value of the tube current. The label "Low mA Ref" in FIG. 5 may represent the fluctuation curve of the real tube current in which the tube current lower bound value is assigned as the set value of the tube current. The label "ΔmA1" in FIG. 5 may represent the first fluctuation difference value. The label "ΔmA2" in FIG. 5 may represent the second fluctuation difference value. The label "$Fil_H$" in FIG. 5 may represent the target upper bound to be calibrated. The label "$Fil_L$" in FIG. 5 may represent the target lower bound to be calibrated.

In block 402, the method may include decreasing the target upper bound to be calibrated and increasing the target lower bound to be calibrated when the target fluctuation difference value is greater than a first fluctuation threshold value, and return to block 401.

When the target fluctuation difference value is greater than the first fluctuation threshold value, it may represent that the difference between the target upper bound to be calibrated and the target lower bound to be calibrated is too large and the real tube current may obviously exceed the requirements of the upper and lower bound of the tube current. In this case, the target upper bound to be calibrated may be decreased and the target lower bound to be calibrated may be increased to reduce the difference between the target upper bound and the target lower bound. Thus, the real tube current may vary according to the requirements of the upper and lower bound of the tube current. Specifically, a fixed adjustment amount ΔFil may be set. When the target fluctuation difference value is greater than the first fluctuation threshold value, the target upper bound to be calibrated may be adjusted as follows: FilH=FilH−ΔFil, and the target lower bound to be calibrated may be adjusted as follows: FilL=FilL−ΔFil.

In block 403, the target upper bound to be calibrated may be increased and the target lower bound to be calibrated may be decreased when the target fluctuation difference value is less than a second fluctuation threshold value, and return to block 401.

When the target fluctuation difference value is less than the second fluctuation threshold value, it may represent that the difference between the target upper bound to be calibrated and the target lower bound to be calibrated is too small and the real tube current may obviously be less than the requirement of the upper bound of the tube current or may obviously be greater than the requirement of the lower bound of the tube current. In this case, the target upper bound to be calibrated may be increased and the target lower bound to be calibrated may be decreased to increase the difference between the target upper bound and the target lower bound. Thus, the real tube current may vary according to the requirements of the upper and lower bound of the tube current. Specifically, a fixed adjustment amount ΔFil may be set. When the target fluctuation difference value is less than the second fluctuation threshold value, the target upper bound to be calibrated may be adjusted as follows: FilH=FilH+ΔFil, and the target lower bound to be calibrated may be adjusted as follows: FilL=FilL−ΔFil.

In block 404, the target upper bound to be calibrated may be identified as the target upper bound value and the target lower bound to be calibrated may be identified as the target lower bound value when the target fluctuation difference value is not greater than the first fluctuation threshold value and not less than the second fluctuation threshold value. The first fluctuation threshold value may be greater than the second fluctuation threshold value.

When the target fluctuation difference value is not greater than the first fluctuation threshold value and not less than the second fluctuation threshold value, it may represent that the difference between the target upper bound to be calibrated and the target lower bound to be calibrated is suitable and the real tube current may meet the requirements of the upper bound and the lower bound of the tube current. In this case, the present target upper bound to be calibrated may be identified as the target upper bound value of the calibrated filament current and the present target lower bound to be calibrated may be identified as the target lower bound value of the calibrated filament current.

In the example shown in FIG. 4, according to the requirements of the upper bound and lower bound of the tube current when the CT tube is in the work mode, the corresponding filament current may be calibrated to obtain the target upper bound value and the target lower bound value. Thus, the tube current controlled by the filament current may fit the requirements of the upper bound and lower bound of the tube current when the CT tube is in the work mode. It may make the control of the filament current more accurate. It may also make a range of radiation dose of the CT tube fully utilized.

Figure 6:
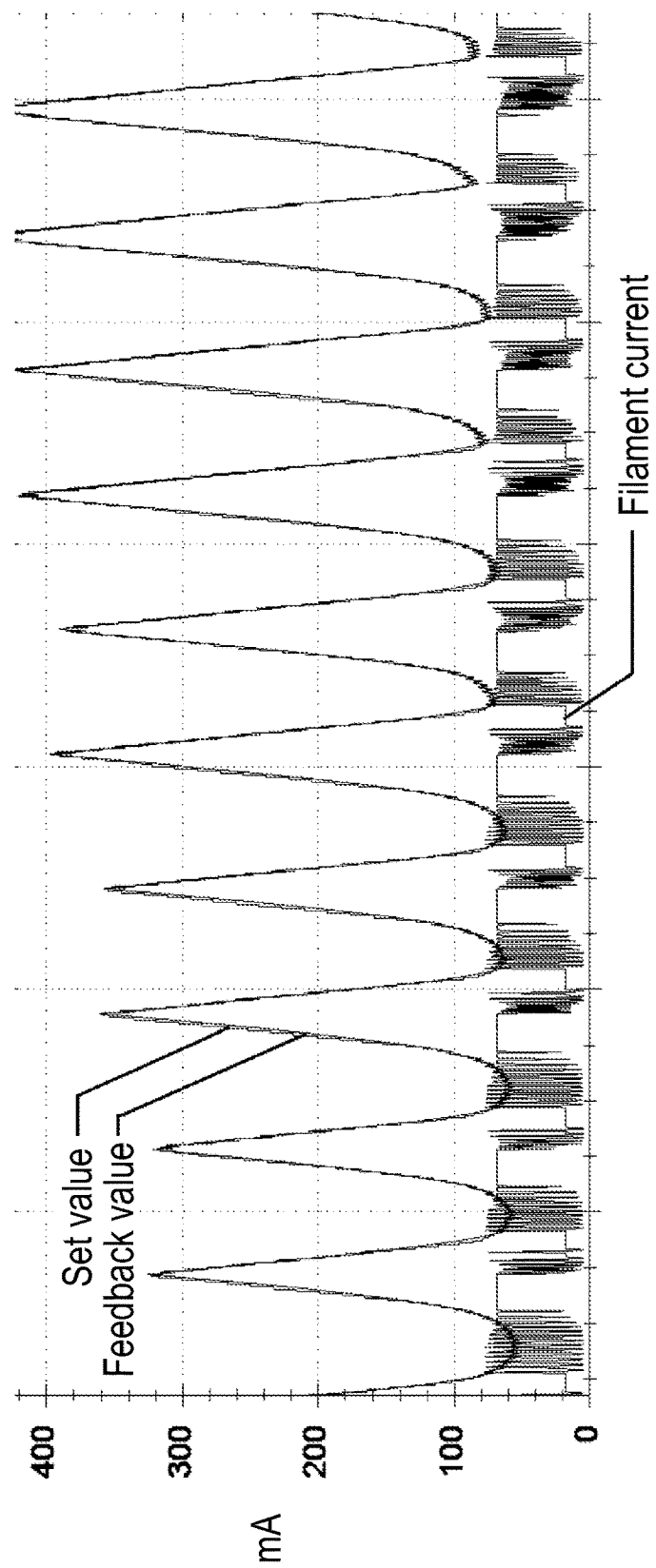
FIG. 6 is a schematic diagram of a current follow effect of a tube current by controlling a filament current, according to an example of the present disclosure.

In the present disclosure, according to the error value between the set value of the tube current and the feedback value, the PWM control chip may control the filament current of the CT tube to directly switch between the target upper bound value and the target lower bound value. When the set value of the tube current may be significantly greater than or less than the feedback value, the PWM control chip may adjust the filament current to the target upper bound value rather than linear increasing. Thus, the real tube current may dramatically increase to follow up the set value of the tube current. When the set value of the tube current may be significantly less than the feedback value and the error value may be less than a second error threshold, the PWM control chip may assign a present filament current as the target lower bound value rather than linear decreasing. Thus, the real tube current may dramatically decrease to follow up the set value of the tube current. In addition, it may solve the problem which the variation speed of the real tube current cannot quickly follow up the variation of the set value of the tube current. FIG. 6 is a schematic diagram of a current follow effect of a tube current by controlling the filament current, according to an example of the present disclosure. As shown in FIG. 6, the curve of the feedback value and the curve of the set value of the tube current are almost identical. It may indicate that, control of the radiation dose is not only fast but also very accurate in the present disclosure.

Figure 7:
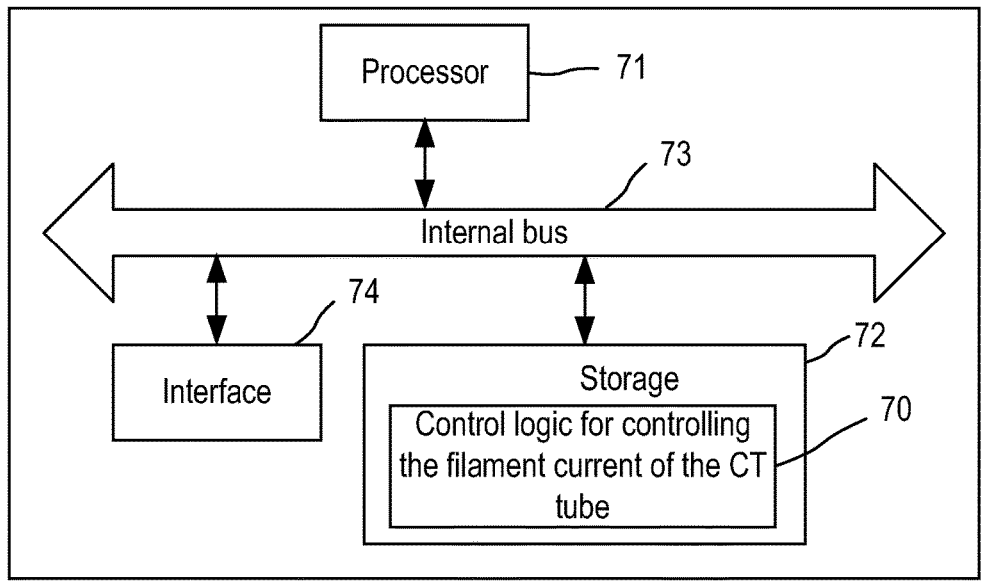
FIG. 7 is a schematic diagram of a hardware structure of a CT apparatus for controlling a filament current of a CT tube, according to an example of the present disclosure.

Corresponding to the aforementioned methods, the present disclosure also provides a CT apparatus for controlling the CT tube filament current. FIG. 7 is a schematic diagram of a hardware structure of the CT apparatus for controlling the filament current of the CT tube according to an example of the present disclosure. As shown in FIG. 7, the CT apparatus may include a processor 71 (e.g., a central processing unit, CPU) and a storage 72, and the storage 72 is accessible by the processor 71 through an internal bus 73. In a possible example, the CT apparatus may further include an external interface 74 for communicating with other devices or modules.

The storage 72 stores the control logic for controlling the filament current of the CT tube 70 of machine readable instructions executable by the processor 71. The storage 72 in which the machine readable instructions are stored may be a non-volatile memory or storage media including by way of example semiconductor memory devices, e.g., EPROM, EEPROM, DRAM and flash memory devices; magnetic disks, e.g., internal hard disks or removable disks; magneto optical disks; and CD ROM and DVD-ROM disks. The processor 71 of the CT apparatus reads the instructions of the corresponding modules of the control logic for controlling the filament current of the CT tube 70 stored in the storage 72 and executes the instructions.

Figure 8:
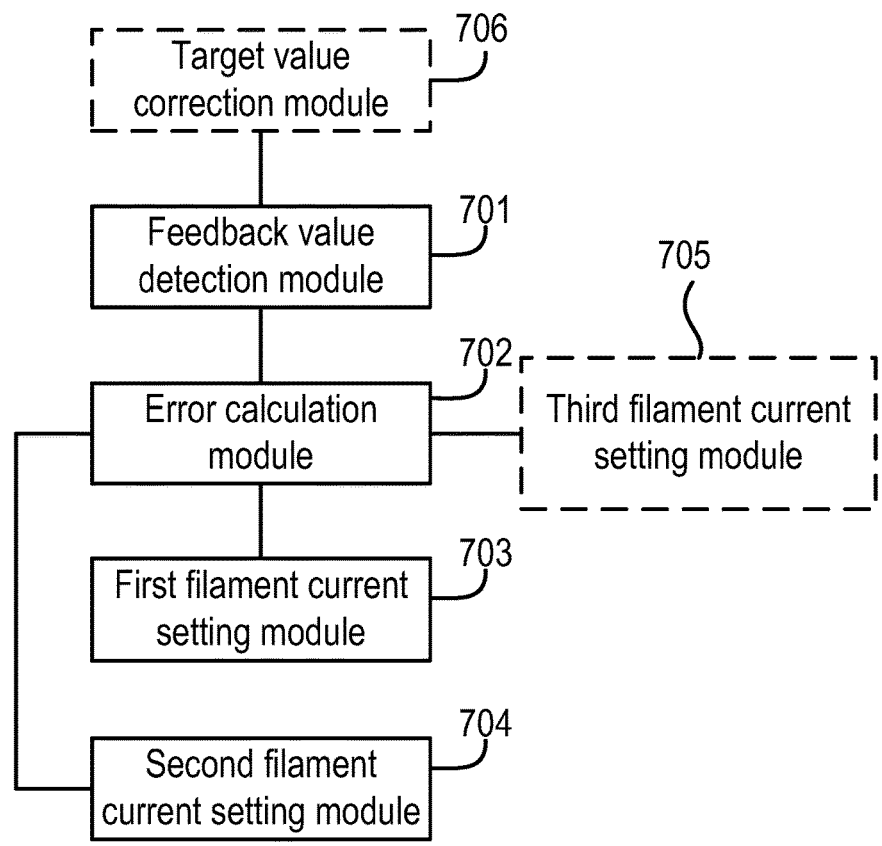
FIG. 8 is a schematic diagram of logical function modules of a control logic for controlling a filament current of a CT tube, according to an example of the present disclosure.

FIG. 8 is a schematic diagram of logical function modules of the control logic for controlling the filament current of the CT tube 70, according to an example of the present disclosure. The control logic for controlling the filament current of the CT tube 70 may include a feedback value detection module 701, an error calculation module 702, a first filament current setting module 703, and a second filament current setting module 704.

The feedback value detection module 701 may be used to detect the present tube current of the CT tube and assign the present tube current to the feedback value.

The error calculation module 702 may be used to calculate a difference between the set value of the tube current and the feedback value and assign the difference to the error value.

The first filament current setting module 703 may be used to set the present filament current to be the target upper bound value when the error value is greater than the first error threshold.

The second filament current setting module 704 may be used to set the present filament current to be the target lower bound value when the error value is less than the second error threshold.

The target upper bound value may be greater than the target lower bound value, the first error threshold may be greater than 0, and the second error threshold may be less than 0.

In other examples of the present disclosure, the control logic for controlling the filament current of the CT tube 70 may include a third filament current setting module 705 and a target value correction module 706.

The third filament current setting module 705 may be used to maintain the present filament current unchanged when the error value is not greater than the first error threshold and not less than the second error threshold.

The target value correction module 706 may be used to assign the filament current value corresponding to the tube current upper bound value of the CT tube in a work mode, to the target upper bound to be calibrated of the filament current. The target value correction module 706 may be used to assign the filament current value corresponding to the tube current lower bound value of the CT tube in the work mode, to the target lower bound to be calibrated of the filament current. The target value correction module 706 may be used to calibrate the target upper bound to be calibrated and the target lower bound to be calibrated to obtain the target upper bound value and the target lower bound value, respectively.

Figure 9:
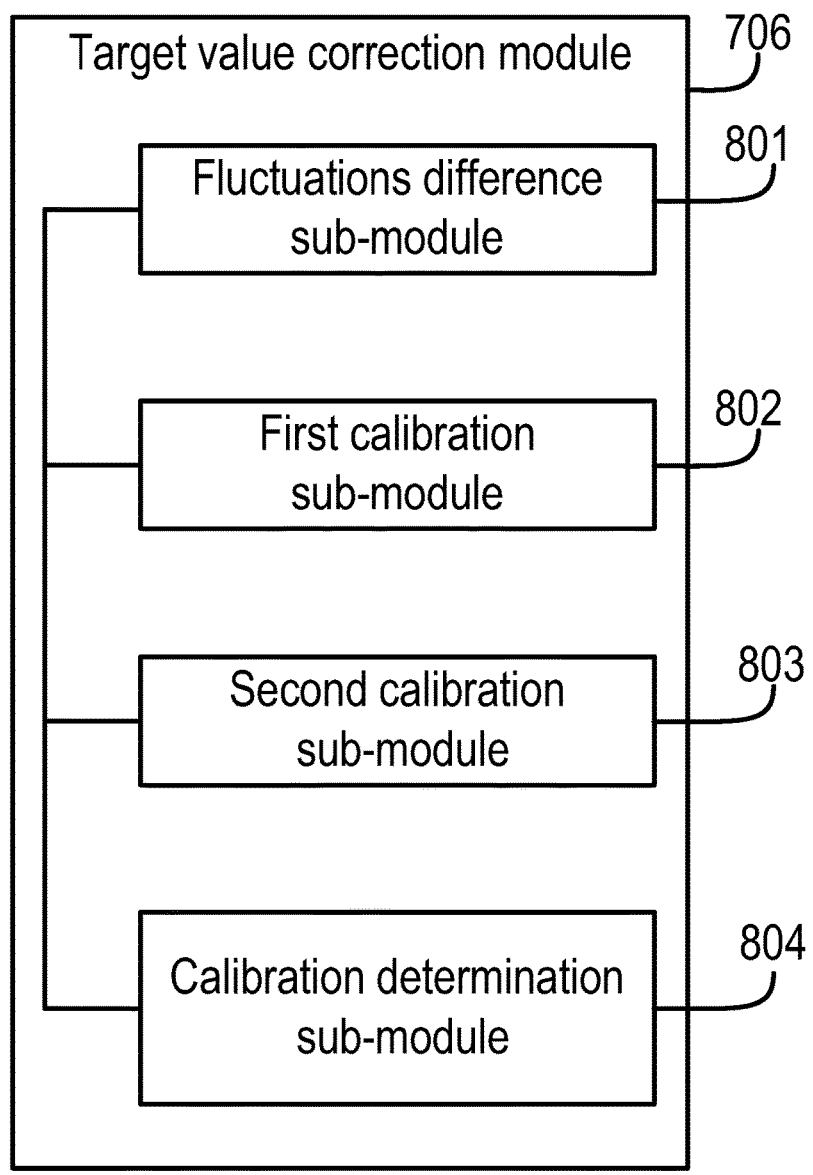
FIG. 9 is a schematic diagram of sub-modules of a target value correction module, according to an example of the present disclosure.

FIG. 9 is a schematic diagram of sub-modules of the target value correction module 706, according to an example of the present disclosure. As shown in FIG. 9, the target value correction module 706 may also include a fluctuations difference sub-module 801, a first calibration sub-module 802, a second calibration sub-module 803, and a calibration determination sub-module 804.

The fluctuations difference sub-module 801 may uses the error value to control the filament current of the CT tube to switch between the target upper bound to be calibrated and the target lower bound to be calibrated, and obtain the target fluctuation difference value of the tube current of the CT tube, wherein the error value is between the set value of the tube current and the feedback value. The target fluctuation difference value may be an absolute value of a maximum difference value between the feedback value and the set value of the tube current in a control process.

The first calibration sub-module 802 may be used to decrease the target upper bound to be calibrated and increase the target lower bound to be calibrated when the target fluctuation difference value is greater than the first fluctuation threshold value, and return to the fluctuations difference sub-module 801.

The second calibration sub-module 803 may be used to increase the target upper bound to be calibrated and decrease the target lower bound to be calibrated when the target fluctuation difference value is less than the second fluctuation threshold value, and return to the fluctuations difference sub-module 801.

The calibration determination sub-module 804 may be used to identify the target upper bound to be calibrated as the target upper bound value and identify the target lower bound to be calibrated as the target lower bound value when the target fluctuation difference value is not greater than the first fluctuation threshold value and the target fluctuation difference value is not less than the second fluctuation threshold value.

The first fluctuation threshold value may be greater than the second fluctuation threshold value.

Figure 10:
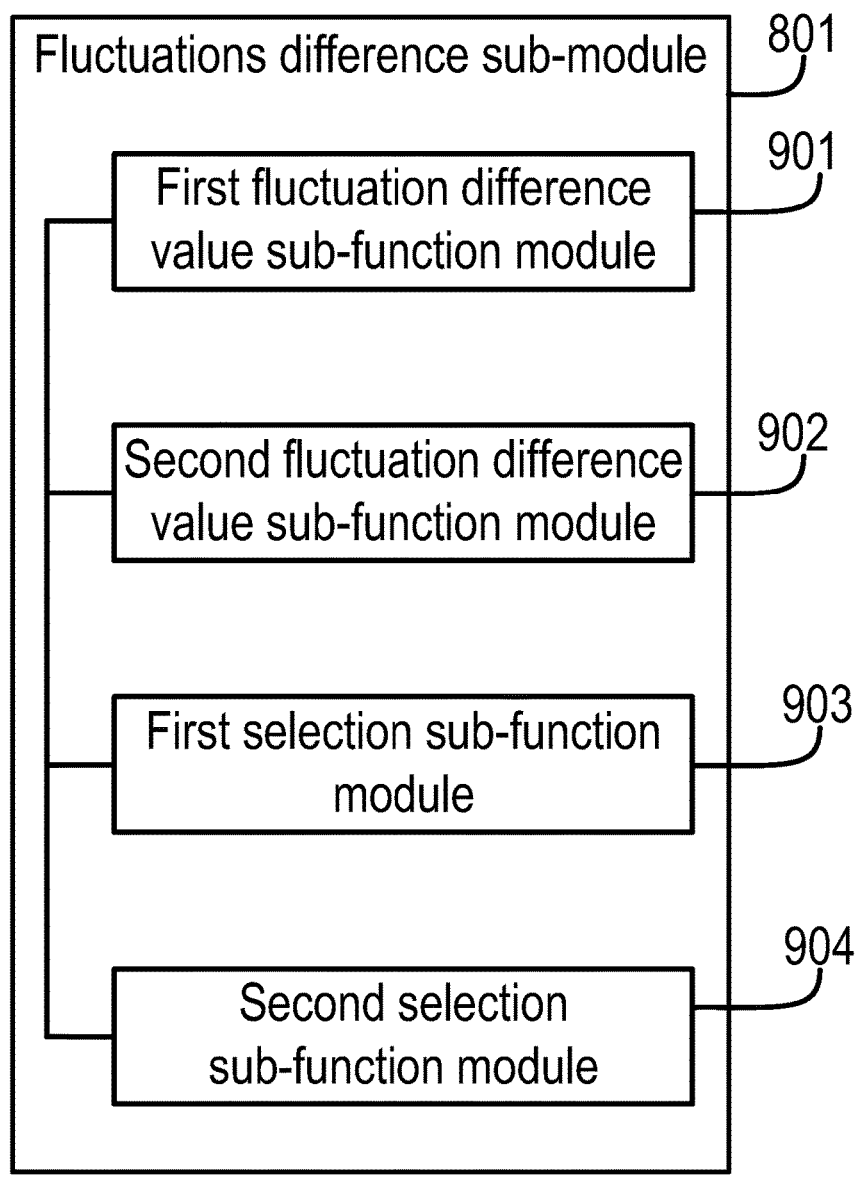
FIG. 10 is a schematic diagram of sub-function modules of a fluctuation difference module 801, according to an example of the present disclosure.

FIG. 10 is a schematic diagram of sub-function modules of the fluctuations difference sub-module 801, according to an example of the present disclosure. The fluctuations difference sub-module 801 may include: a first fluctuation difference value sub-function module 901, a second fluctuation difference value sub-function module 902, a first selection sub-function module 903, and a second selection sub-function module 904.

The first fluctuation difference value sub-function module 901 assigns the tube current upper bound value of the CT tube during the work mode to the set value of the tube current. The first fluctuation difference value sub-function module 901 may use the error value to control the filament current of the CT tube to switch between the target upper bound to be calibrated and the target lower bound to be calibrated, and obtain the first fluctuation range of the tube current of the CT tube, wherein the error value is between the tube current upper bound value and the feedback value. The first fluctuation difference value sub-function module 901 may calculate the first fluctuation difference value of the first fluctuation range.

The second fluctuation difference value sub-function module 902 may assign the tube current lower bound value of the CT tube being in the work mode to the set value of the tube current. The second fluctuation difference value sub-function module 902 may use the error value to control the filament current of the CT tube to switch between the target upper bound to be calibrated and the target lower bound to be calibrated, and obtain a second fluctuation range of the tube current of the CT tube, wherein the error value is between the tube current lower bound value and the feedback value. The second fluctuation difference value sub-function module 902 may calculate a second fluctuation difference value of the second fluctuation range.

The first selection sub-function module 903 may be used to select the first fluctuation difference value to be the target fluctuation difference value when first fluctuation difference value is greater than the second fluctuation difference value.

The second selection sub-function module 904 may be used to select the second fluctuation difference value to be the target fluctuation difference value when first fluctuation difference value is not greater than the second fluctuation difference value.

The following technology may be implemented in software which is described the operation of the control logic for controlling the filament current of the CT tube 70. The storage 72 stores the control logic for controlling the filament current of the CT tube 70 of machine readable instructions executable by the processor 71. The processor 71 of the CT apparatus reads the instructions of the corresponding modules of the control logic for controlling the filament current of the CT tube 70 stored in the storage 72 and executes the instructions.

The instructions executed by the processor 71 may cause the processor 71 to perform the following operations:

The processor 71 may detect a present tube current of the CT tube and assign the present tube current to a feedback value.

The processor 71 may calculate a difference between a set value of the tube current and the feedback value and assign the difference to an error value.

When the error value is greater than the first error threshold, the processor 71 may set a present filament current to be the target upper bound value.

When the error value is less than the second error threshold, the processor 71 may set the present filament current to be the target lower bound value.

The target upper bound value may be greater than the target lower bound value, the first error threshold may be greater than 0, and the second error threshold may be less than 0.

The instructions executed by the processor 71 may cause the processor 71 to perform the following operation.

The processor 71 may maintain the present filament current unchanged when the error value is not greater than the first error threshold and not less than the second error threshold.

The instructions executed by the processor 71 may further cause the processor 71 to perform the following operations.

The processor 71 may assign a filament current value which is corresponding to the tube current upper bound value of the CT tube during a work mode to the target upper bound to be calibrated of the filament current. The processor 71 may assign the filament current value which is corresponding to the tube current lower bound value of the CT tube during the work mode to the target lower bound to be calibrated of the filament current. The processor 71 may calibrate the target upper bound to be calibrated and the target lower bound to be calibrated to obtain the target upper bound value and the target lower bound value, respectively.

Further, the instructions executed by the processor 71 may cause the processor 71 to perform the following operations:

The processor 71 may use the error value to control the filament current of the CT tube to switch between the target upper bound to be calibrated and the target lower bound to be calibrated, and obtain a target fluctuation difference value of the tube current of the CT tube, wherein the error value is between the set value of the tube current and the feedback value. The target fluctuation difference value may be an absolute value of a maximum difference value between the feedback value and the set value of the tube current in the control process.

When the target fluctuation difference value is greater than a first fluctuation threshold value, the processor 71 may decrease the target upper bound to be calibrated and increase the target lower bound to be calibrated.

When the target fluctuation difference value is less than a second fluctuation threshold value, the processor 71 may increase the target upper bound to be calibrated and decrease the target lower bound to be calibrated.

When the target fluctuation difference value is not greater than the first fluctuation threshold value and the target fluctuation difference value is not less the second fluctuation threshold value, the processor 71 may identify the target upper bound to be calibrated as the target upper bound value and identify the target lower bound to be calibrated as the target lower bound value.

The first fluctuation threshold value is greater than the second fluctuation threshold value.

The instructions executed by the processor 71 may cause the processor 71 to perform the following operations:

The processor 71 may assign the tube current upper bound value to the set value of the tube current. The processor 71 may use the error value to control the filament current of the CT tube to switch between the target upper bound to be calibrated and the target lower bound to be calibrated, and obtain the first fluctuation range of the tube current of the CT tube, wherein the error value is between the tube current upper bound value and the feedback value. The processor 71 may calculate the first fluctuation difference value of the first fluctuation range.

The processor 71 may assign the tube current lower bound value to the set value of the tube current. The processor 71 may use the error value to control the filament current of the CT tube to switch between the target upper bound to be calibrated and the target lower bound to be calibrated, and obtain a second fluctuation range of the tube current of the CT tube, wherein the error value is between the tube current lower bound value and the feedback value. The processor 71 may calculate a second fluctuation difference value of the second fluctuation range.

When first fluctuation difference value is greater than the second fluctuation difference value, the processor 71 may select the first fluctuation difference value to be the target fluctuation difference value.

When first fluctuation difference value is not greater the second fluctuation difference value, the processor 71 may select the second fluctuation difference value to be the target fluctuation difference value.

The above are only preferred examples of the present invention and are not intended to limit the invention. Within the spirit and principles of the present invention, any changes made, equivalent replacement, or improvement in the protection of the present invention should contain within the range.

The methods, processes and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for controlling a filament current of a computed tomography (CT) tube, comprising:
   detecting a present tube current of the CT tube and assigning the present tube current to a feedback value;
   calculating a difference between a set value of a tube current and the feedback value and assigning the difference to an error value;
   setting a present filament current to be a target upper bound value when the error value is greater than a first error threshold; and
   setting the present filament current to be a target lower bound value when the error value is less than a second error threshold;
   wherein the target upper bound value is greater than the target lower bound value, the first error threshold is greater than 0, and the second error threshold is less than 0.

2. The method according to claim 1, further comprising:
   maintaining the present filament current unchanged when the error value is less than or equal to the first error threshold and the error value is greater than or equal to the second error threshold.

3. The method according to claim 1, further comprising:
   assigning a filament current value which corresponds to a tube current upper bound value of the CT tube in a work mode to a target upper bound to be calibrated of a filament current;
   assigning a filament current value which corresponds to a tube current lower bound value of the CT tube in the work mode to a target lower bound to be calibrated of the filament current;
   calibrating the target upper bound to be calibrated to obtain the target upper bound value; and
   calibrating the target lower bound to be calibrated to obtain the target lower bound value.

4. The method according to claim 3, wherein said calibrating the target upper bound to be calibrated and said calibrating the target lower bound to be calibrated comprise:
   using the error value between the set value of the tube current and the feedback value to control the filament current of the CT tube to switch between the target upper bound to be calibrated and the target lower bound to be calibrated to obtain a target fluctuation difference value of the tube current of the CT tube;
   decreasing the target upper bound to be calibrated and increasing the target lower bound to be calibrated when the target fluctuation difference value is greater than a first fluctuation threshold value;
   increasing the target upper bound to be calibrated and decreasing the target lower bound to be calibrated when the target fluctuation difference value is less than a second fluctuation threshold value; and
   identifying the target upper bound to be calibrated as the target upper bound value and identifying the target lower bound to be calibrated as the target lower bound value when the target fluctuation difference value is less than or equal to the first fluctuation threshold value and the target fluctuation difference value is greater than or equal to the second fluctuation threshold value;
   wherein the first fluctuation threshold value is greater than the second fluctuation threshold value.

5. The method according to claim 4, wherein the target fluctuation difference value is an absolute value of a maximum difference value between the feedback value and the set value of the tube current in a control process.

6. The method according to claim 5, wherein said using the error value between the set value of the tube current and the feedback value to control the filament current of the CT tube to switch between the target upper bound to be calibrated and the target lower bound to be calibrated to obtain the target fluctuation difference value of the tube current of the CT tube comprises:
   assigning the tube current upper bound value of the CT tube being in the work mode to the set value of the tube current, using the error value between the tube current upper bound value and the feedback value to control the filament current of the CT tube to switch between the target upper bound to be calibrated and the target lower bound to be calibrated to obtain a first fluctuation range of the tube current of the CT tube, and calculating a first fluctuation difference value of the first fluctuation range;
   assigning the tube current lower bound value of the CT tube being in the work mode to the set value of the tube current, using the error value between the tube current lower bound value and the feedback value to control the filament current of the CT tube to switch between the target upper bound to be calibrated and the target lower bound to be calibrated to obtain a second fluctuation range of the tube current of the CT tube, and calculating a second fluctuation difference value of the second fluctuation range;
   selecting the first fluctuation difference value to be the target fluctuation difference value when the first fluctuation difference value is greater than the second fluctuation difference value; and
   selecting the second fluctuation difference value to be the target fluctuation difference value when the first fluctuation difference value is less than or equal to the second fluctuation difference value.

7. An apparatus for controlling a filament current of a computed tomography (CT) tube, comprising:
   a processor, wherein the processor reads and executes machine readable instructions of a control logic for controlling a filament current stored in a storage and is caused to:
      detect a present tube current of the CT tube and assign the present tube current to a feedback value;
      calculate a difference between a set value of a tube current and the feedback value and assign the difference to an error value;
      set a present filament current to be a target upper bound value when the error value is greater than a first error threshold; and
      set the present filament current to be a target lower bound value when the error value is less than a second error threshold;
      wherein the target upper bound value is greater than the target lower bound value, the first error threshold is greater than 0, and the second error threshold is less than 0.

8. The apparatus according to claim 7, wherein the machine readable instructions further cause the processor to:
   maintain the present filament current unchanged when the error value is less than or equal to the first error threshold and the error value is greater than or equal to the second error threshold.

9. The apparatus according to claim 7, wherein the machine readable instructions further cause the processor to:

assign a filament current value which corresponds to a tube current upper bound value of the CT tube being in a work mode to a target upper bound to be calibrated of the filament current;

assign a filament current value which corresponds to a tube current lower bound value of the CT tube being in the work mode to a target lower bound to be calibrated of the filament current;

calibrate the target upper bound to be calibrated to obtain the target upper bound value; and calibrate the target lower bound to be calibrated to obtain the target lower bound value.

10. The apparatus according to claim 9, wherein the machine readable instructions further cause the processor to:

use the error value between the set value of the tube current and the feedback value to control the filament current of the CT tube to switch between the target upper bound to be calibrated and the target lower bound to be calibrated to obtain a target fluctuation difference value of the tube current of the CT tube;

decrease the target upper bound to be calibrated and increase the target lower bound to be calibrated when the target fluctuation difference value is greater than a first fluctuation threshold value;

increase the target upper bound to be calibrated and decrease the target lower bound to be calibrated when the target fluctuation difference value is less than a second fluctuation threshold value; and identify the target upper bound to be calibrated as the target upper bound value and identify the target lower bound to be calibrated as the target lower bound value when the target fluctuation difference value is less than or equal to the first fluctuation threshold value and the target fluctuation difference value is greater than or equal to the second fluctuation threshold value;

wherein the first fluctuation threshold value is greater than the second fluctuation threshold value.

11. The apparatus according to claim 10, wherein the target fluctuation difference value is an absolute value of a maximum difference value between the feedback value and the set value of the tube current in a control process.

12. The apparatus according to claim 11, wherein the machine readable instructions further cause the processor to:

assign the tube current upper bound value of the CT tube in the work mode to the set value of the tube current, use the error value between the tube current upper bound value and the feedback value to control the filament current of the CT tube to switch between the target upper bound to be calibrated and the target lower bound to be calibrated to obtain a first fluctuation range of the tube current of the CT tube, and calculate a first fluctuation difference value of the first fluctuation range;

assign the tube current lower bound value of the CT tube being in the work mode to the set value of the tube current, use the error value between the tube current lower bound value and the feedback value to control the filament current of the CT tube to switch between the target upper bound to be calibrated and the target lower bound to be calibrated to obtain a second fluctuation range of the tube current of the CT tube, and calculate a second fluctuation difference value of the second fluctuation range;

select the first fluctuation difference value to be the target fluctuation difference value when the first fluctuation difference value is greater than the second fluctuation difference value; and select the second fluctuation difference value to be the target fluctuation difference value when the first fluctuation difference value is less than or equal to the second fluctuation difference value.

\* \* \* \* \*